(12) United States Patent
Peterman (10) Patent No.: US 7,789,898 B2
(45) Date of Patent: Sep. 7, 2010

(54) TRANSVERSE PROCESS/LAMINAR SPACER

(75) Inventor: Marc Peterman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 416 days.

(21) Appl. No.: 11/107,171

(22) Filed: Apr. 15, 2005

(65) Prior Publication Data

US 2006/0235387 A1 Oct. 19, 2006

(51) Int. Cl.
*A61B 17/88* (2006.01)
(52) U.S. Cl. .................................... 606/279; 606/246
(58) Field of Classification Search ................ 606/61, 606/279, 246–249; 623/16.11, 17.11–17.16
See application file for complete search history.

(56) References Cited

U.S. PATENT DOCUMENTS

| | | | |
|---|---|---|---|
| 2,677,369 A | 5/1954 | Knowles | |
| 2,774,350 A | 12/1956 | Cleveland | |
| 3,648,691 A | 3/1972 | Lumb et al. | |
| 3,693,616 A | 9/1972 | Roaf et al. | |
| 4,011,602 A | 3/1977 | Rybicki et al. | |
| 4,257,409 A | 3/1981 | Bacal et al. | |
| 4,269,178 A * | 5/1981 | Keene | 606/276 |
| 4,422,451 A | 12/1983 | Kalamchi | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 4,913,134 A | 4/1990 | Luque | |
| 5,010,879 A * | 4/1991 | Moriya et al. | 606/276 |
| 5,011,484 A | 4/1991 | Breard | |
| 5,047,055 A | 9/1991 | Bao et al. | |
| 5,092,866 A | 3/1992 | Breard et al. | |
| 5,116,334 A * | 5/1992 | Cozad et al. | 606/250 |
| 5,201,734 A | 4/1993 | Cozad et al. | |
| 5,306,275 A | 4/1994 | Bryan | |
| 5,360,430 A | 11/1994 | Lin | |
| 5,366,455 A | 11/1994 | Dove et al. | |
| 5,415,661 A | 5/1995 | Holmes | |

(Continued)

FOREIGN PATENT DOCUMENTS

DE 2821678 11/1979

(Continued)

OTHER PUBLICATIONS

Medtronic Sofamor Danek, CD Horizon Legacy 5.5 Spinal System—Deformity Surgical Technique, 2004.

(Continued)

*Primary Examiner*—Eduardo C Robert
*Assistant Examiner*—Tara R Carter
(74) *Attorney, Agent, or Firm*—Coats and Bennett, P.L.L.C.

(57) ABSTRACT

An inter-transverse process spacer system comprises a first spacer device. The first spacer device comprises opposing end portions. The first spacer device is adapted for insertion between a first pair of adjacent transverse processes, and the opposing end portions of the first spacer device are adapted to engage the first pair of adjacent transverse processes. The inter-transverse process spacer system further comprises a first connection device connected to the first spacer device and adapted to engage at least one of the first pair of adjacent transverse processes.

12 Claims, 4 Drawing Sheets

U.S. PATENT DOCUMENTS

| | | |
|---|---|---|
| 5,437,672 A | 8/1995 | Alleyne |
| 5,454,812 A | 10/1995 | Lin |
| 5,496,318 A * | 3/1996 | Howland et al. ............... 606/61 |
| 5,609,592 A | 3/1997 | Brumfield et al. |
| 5,609,634 A | 3/1997 | Voydeville |
| 5,628,756 A | 5/1997 | Barker, Jr. et al. |
| 5,645,599 A * | 7/1997 | Samani .................... 623/17.16 |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,725,582 A * | 3/1998 | Bevan et al. ................ 606/263 |
| 5,810,815 A | 9/1998 | Morales |
| 5,810,818 A * | 9/1998 | Errico et al. .................. 606/61 |
| 5,836,948 A * | 11/1998 | Zucherman et al. ........... 606/61 |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,066,140 A * | 5/2000 | Gertzbein et al. ............. 606/61 |
| 6,068,630 A | 5/2000 | Zucherman et al. |
| 6,132,464 A | 10/2000 | Martin |
| 6,293,949 B1 | 9/2001 | Justis et al. |
| 6,312,431 B1 | 11/2001 | Asfora |
| 6,336,930 B1 | 1/2002 | Stalcup et al. |
| 6,352,537 B1 | 3/2002 | Strnad |
| 6,364,883 B1 | 4/2002 | Santilli |
| 6,402,750 B1 | 6/2002 | Atkinson et al. |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,582,433 B2 | 6/2003 | Yun |
| 6,626,944 B1 * | 9/2003 | Taylor ..................... 623/17.16 |
| 6,645,207 B2 | 11/2003 | Dixon et al. |
| 6,695,842 B2 | 2/2004 | Zucherman et al. |
| 6,709,435 B2 | 3/2004 | Lin |
| 6,723,126 B1 | 4/2004 | Berry |
| 6,733,534 B2 | 5/2004 | Sherman |
| 6,752,831 B2 * | 6/2004 | Sybert et al. ............. 623/13.17 |
| 6,761,720 B1 * | 7/2004 | Senegas ....................... 606/61 |
| 6,835,205 B2 | 12/2004 | Atkinson et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,252,673 B2 | 8/2007 | Lim |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 2002/0095154 A1 | 7/2002 | Atkinson et al. |
| 2002/0143331 A1 | 10/2002 | Zucherman et al. |
| 2003/0040746 A1 | 2/2003 | Mitchell et al. |
| 2003/0065330 A1 | 4/2003 | Zucherman et al. |
| 2003/0153915 A1 | 8/2003 | Nekozuka et al. |
| 2003/0216736 A1 | 11/2003 | Robinson et al. |
| 2004/0097931 A1 | 5/2004 | Mitchell |
| 2004/0106995 A1 | 6/2004 | Le Couedic et al. |
| 2004/0181282 A1 | 9/2004 | Zucherman et al. |
| 2004/0243239 A1 | 12/2004 | Taylor |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Feree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0136060 A1 | 6/2006 | Taylor |
| 2006/0149242 A1* | 7/2006 | Kraus et al. ................... 606/61 |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1* | 11/2006 | Petrini et al. .................. 606/61 |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0112350 A1* | 5/2007 | Deneuvillers et al. ......... 606/61 |
| 2007/0162000 A1 | 7/2007 | Perkins |
| 2007/0198091 A1 | 8/2007 | Boyer et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2008/0161818 A1 | 7/2008 | Kloss et al. |

FOREIGN PATENT DOCUMENTS

| | | |
|---|---|---|
| DE | 2821678 A1 | 11/1979 |
| EP | 0322334 B1 | 2/1992 |
| EP | 1138268 | 4/2001 |
| EP | 1330987 A1 | 7/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 | 7/2000 |
| FR | 2799948 A1 | 4/2001 |
| FR | 2828398 | 8/2001 |
| FR | 2861285 A1 * | 4/2005 |
| GB | 780652 | 12/1957 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | 2004084743 A1 | 10/2004 |

| WO | WO 2004084743 A1 * | 10/2004 |
| WO | WO 2005/009300 A1 | 2/2005 |
| WO | 2005/037150 | 4/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

Posterior Spinal Instrumentation for Thoracolumbar Tumor and Trauma Reconstruction, Seminars in Spine Surgery, vol. 9, No. 3, Sep. 1997, pp. 260-277.

Reduction and Fixation of Late Diagnosed Lower Cervical Spine Dislocations Using the Daab Plate, Archives of Orthopaedic and Traumatic Surgery, 1984, pp. 353-355.

Posterior Spinal Fusion Using Internal Fixation with the Daab Plate, Act. Orthop. Scand. 55, pp. 310-314, 1984.

The Value of the Wilson Plate in Spinal Fusion, M.C. Cobey, M.D., May 1971.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dispositivo Intervertebrale Ammortizzante DIAM, date unknown, p. 1.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirurgia, Advanced Peripheral Nerve Surgery and Minimal Invasive Spinal Surgery, Alexandre et al., eds., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille Tecnica Operatoria Per II Posizionamento Della Protesi DIAM, date unknown, pp. 1-3.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wallis Operative Technique: Surgical Procedure for Treatment of Degenerative Disc Disease (DDD) of Lumbar Spine, date unknown, pp. 1-24, Spine Next, an Abbott Laboratories company, Bordeaux, France.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

TRANSVERSE PROCESS/LAMINAR SPACER

BACKGROUND

Severe back pain and nerve damage may be caused by injured, degraded, or diseased spinal joints and particularly, spinal discs. Current methods of treating these damaged spinal discs may include vertebral fusion, nucleus replacements, or motion preservation disc prostheses. Disc deterioration and other spinal deterioration may cause spinal stenosis, a narrowing of the spinal canal and/or the intervertebral foramen, that causes pinching of the spinal cord and associated nerves. Current methods of treating spinal stenosis include laminectomy or facet resection. Alternative and potentially less invasive options are needed to provide spinal pain relief.

SUMMARY

In one embodiment of the present disclosure, an inter-transverse process spacer system comprises a first spacer device. The first spacer device comprises opposing end portions. The first spacer device is adapted for insertion between a first pair of adjacent transverse processes, and the opposing end portions of the first spacer device are adapted to engage the first pair of adjacent transverse processes. The inter-transverse process spacer system further comprises a first connection device connected to the first spacer device and adapted to engage at least one of the first pair of adjacent transverse processes.

In another embodiment, an inter-laminar spacer system comprises a first connection device adapted to engage a lamina of a first vertebra and a second connection device adapted to engage a lamina of a second vertebra. The inter-laminar spacer system further comprises a first lamina spacer extending between the first and second connection devices.

In another embodiment, a method of spinal decompression comprises accessing a pair of transverse processes and inserting a spacer device between the pair of transverse processes. The method further comprises engaging a connection device with the spacer device and at least one of the pair of transverse processes.

In another embodiment of the present disclosure, a method of decompressing a spinal joint comprises accessing an inter-laminar space between first and second lamina and inserting a spacer system into the interlaminar space. The method further comprises connecting the spacer system to inner and outer faces of the first lamina.

DETAILED DESCRIPTION

The present disclosure relates generally to the field of orthopedic surgery, and more particularly to systems and methods for decompressing a spinal joint. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 1:
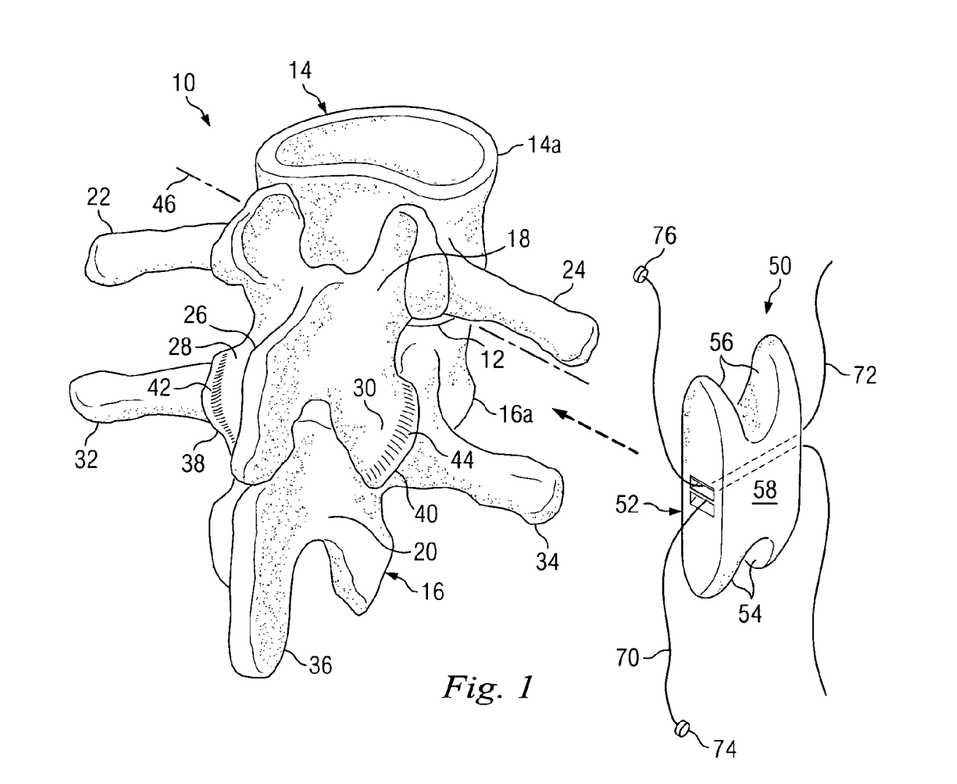
FIG. 1 is a perspective view of a vertebral column with an inter-transverse process spacer system according to one embodiment of the present disclosure.

Referring first to FIG. 1, the numeral 10 refers to a vertebral joint which includes an intervertebral disc 12 extending between vertebrae 14, 16. The vertebra 14 includes a lamina 18, and the vertebra 16 includes a lamina 20. The vertebrae 14, 16 also include vertebral bodies 14a, 16a, respectively. The vertebra 14 further includes transverse processes 22, 24; a spinous process 26; and caudal articular processes 28, 30. The vertebra 16 further includes transverse processes 32, 34; a spinous process 36; and rostral articular processes 38, 40. Although the illustration of FIG. 1 generally depicts the vertebral joint 10 as a lumbar vertebral joint, it is understood that the devices, systems, and methods of this disclosure may also be applied to all regions of the vertebral column, including the cervical and thoracic regions. Furthermore, the devices, systems, and methods of this disclosure may be used in non-spinal orthopedic applications.

A facet joint 42 is formed, in part, by the adjacent articular processes 28, 38. A facet joint 44 is formed, in part, by the adjacent articular processes 30, 40. Facet joints may also be termed zygapophyseal joints. A healthy facet joint includes a facet capsule extending between the adjacent articular processes. The facet capsule comprises cartilage and synovial fluid to permit the articulating surfaces of the articular processes to remain lubricated and glide over one another. The type of motion permitted by the facet joints is dependent on the region of the vertebral column. For example, in a healthy lumbar region, the facet joints limit rotational motion but permit greater freedom for flexion, extension, and lateral bending motions. By contrast, in a healthy cervical region of the vertebral column, the facet joints permit rotational motion as well as flexion, extension, and lateral bending motions. As the facet joint deteriorates, the facet capsule may become compressed and worn, losing its ability to provide a smooth, lubricated interface between the articular surfaces of the articular processes. This may cause pain and limit motion at the affected joint. Facet joint deterioration may also cause inflammation and enlargement of the facet joint which may, in turn, contribute to spinal stenosis. Removal of an afflicted articular process may result in abnormal motions and loading on the remaining components of the joint. The embodiments described below may be used to decompress a deteriorated facet joint and/or restore more natural motion constraint to a resected joint.

Injury, disease, and deterioration of the intervertebral disc 12 may also cause pain and limit motion. In a healthy intervertebral joint, the intervertebral disc permits rotation, lateral bending, flexion, and extension motions. An axis of flexion 46 may extend between the vertebral bodies 14a, 16a and through the intervertebral disc 12. As the intervertebral joint deteriorates, the intervertebral disc may become compressed, displaced, or herniated, resulting in excess pressure in other areas of the spine, particularly the posterior bony elements of the afflicted vertebrae. This deterioration may lead to spinal stenosis. The embodiments described below may restore more natural spacing to the posterior bony elements of the vertebrae, decompress an intervertebral disc, and/or may relieve spinal stenosis.

Figure 3:
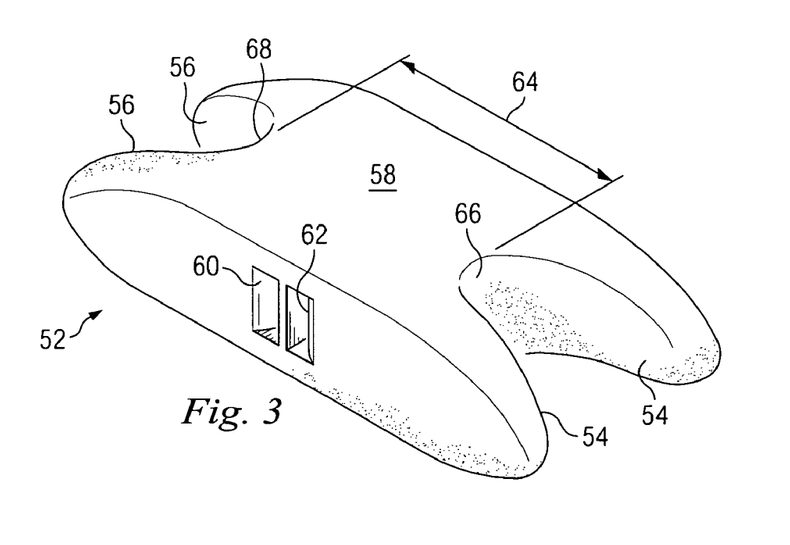
FIG. 3 is a perspective view of a component of the spacer system of FIG. 1.
Figure 4:
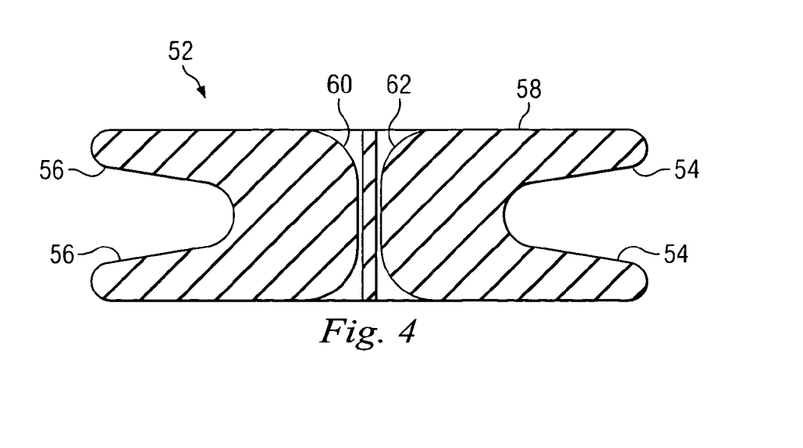
FIG. 4 is a sectional view of the component of FIG. 3.

Referring still to FIG. 1, in one embodiment, a spacer system 50 may be used to support the transverse processes 24, 34; decompress the disc 12 and the facet joint 44; and/or relieve stenosis. The spacer system 50 includes a spacer device 52 which may be monolithically formed of an elastic, multi-directionally flexible material such as silicone, polyurethane, or hydrogel. The spacer device 52 may include two pairs of legs 54, 56 integrally formed with and extending from a cross member 58. As shown in greater detail in FIGS. 3 and 4, the cross member 58 may comprise transverse conduits 60, 62. The openings of the conduits 60, 62 may be widened and curved to minimize sharp edges that could present a point of wear. The internal faces of the legs 54 are angled to converge toward a recessed area 66, and the internal faces of the legs 56 are angled to converge toward a recessed area 68. The cross member 58 has a thickness 64 which may be slightly greater than the inter-transverse process space between the processes 24, 34 when the vertebra 14, 16 are in a natural position. For example, the cervical and lumbar regions of the vertebral column may be in lordosis when in a natural position.

Figure 2:
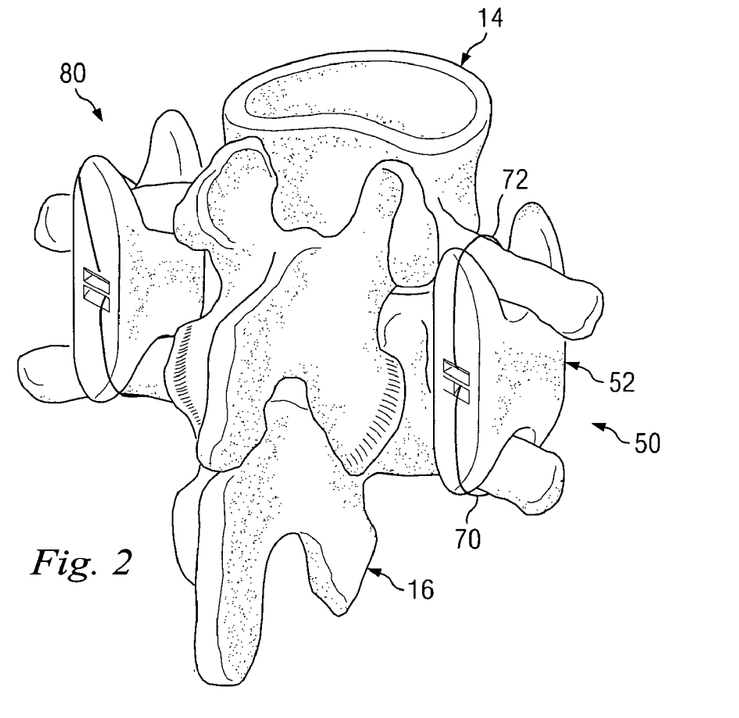
FIG. 2 is an assembled perspective view of the spacer system of FIG. 1.

Referring now to FIGS. 1 and 2, in this embodiment, the spacer system 50 further includes connection devices such as cables 70, 72 which extend through the transverse conduits 62, 64, respectively, of the cross member 58. At least one end of each of the cables 70, 72 may be attached to stopper devices 74, 76, respectively. The connection devices may be either elastic or inelastic and able to carry tensile forces. They may be formed, for example, of biocompatible reinforcing materials such as wire, cable, cord, bands, tape, or sheets. They may have a braided, knitted, or woven construction.

A surgical procedure to implant the spacer system 50 may be ultra minimally invasive. Using a posterior, posterolateral, lateral, anterolateral or anterior approach, a small incision may be created in the patient's skin. The transverse processes 24, 34 may be visualized directly or with radiographic assistance. The spacer device 52 may be compressed and inserted between the transverse processes 24, 34. The spacer device 52 may then expand slightly so that the recess 68 comes into firm contact with the transverse process 24 and the recess 66 comes into firm contact with the transverse process 34. The cross member 58 may remain slightly compressed after implantation so that the recesses 66, 68 may continue to exert pressure on the transverse processes 34, 24, respectively, minimizing the opportunity for the spacer device 52 to become dislodged. The compression of the cross member 58 may bias the legs 56 to compress together, creating a firm grip on the transverse process 24. This holding action, together with the flexibility of the device 52, minimizes friction and the associated material and bone wear. The legs 54 may, likewise, grip transverse process 34.

The connection device 72, led for example by a needle, may be inserted through the conduit 60 and around the transverse process 24. The connection device 72 may then be inserted through the stopper 76. The location of the spacer device 52 may still be adjusted while the connection device 72 is relatively loose. For example, the spacer device 52 may be placed close to the base of the transverse processes 24, 34, near the vertebral bodies 14a, 16a, to reduce the torsional forces placed on the spacer device by the transverse processes. With the spacer device 52 in the desired position, the connection device 72 may be tightened, and anchored to the stopper device 76. The stopper device 76 may thus anchor both ends of the connection device 72. The connection device 70 may similarly anchor the spacer device to the transverse process 34.

In certain anatomies, the spacer system 50 may be used alone to provide decompression to a single targeted facet joint or to relieve pressure on a particular side of the intervertebral disc, such as a herniation area. But, as shown in FIG. 2, a second spacer system 80 may be installed on the opposite lateral side from the spacer system 50, between transverse processes 22, 32. The spacer system 80, when used in conjunction with the spacer system 50, may provide more balanced support and equalized decompression. The spacer system 80 may be substantially similar to system 50 and therefore will not be described in detail.

The spacer system 50, as installed, may axially separate the vertebrae 14, 16, relieving pressure on the intervertebral disc 12 and the facet joint 44 and reducing wear and further degeneration. The spacer device 52 may also dampen the forces on the intervertebral disc 12 and facet joint 44 during motion such as flexion and extension. Because the spacer device 52 may be positioned relatively close to the natural axis of flexion 46, the spacer system 50 may be less likely to induce kyphosis as compared to systems that rely upon inter-spinous process devices to provide decompression. Additionally, the system 50 may be installed minimally invasively with less dissection than the inter-spinous process devices of the prior art. Furthermore, an inter-transverse process system can be used on each lateral side of the vertebrae 14, 16, and may provide greater and more balanced decompression than the single inter-spinous process devices of the prior art.

In an alternative embodiment, the conduits through the spacer device may be omitted and the connection devices attached to other connection points on the spacer device such as side handles. The connection device may extend through or into one or both of the transverse processes. In still another alternative, the connection device may be eliminated and the spacer device held in place by the compressive forces of the transverse processes. The connection device may also take the form of a clamp, spike, threaded connection or any other type of mechanical or adhesive connection for attaching devices to bone.

In another alternative embodiment, the spacer device may be shaped to address various patient anatomies and afflictions. In one embodiment, the legs of the spacer device may be angled such that the spacer device provides not only cephalad-caudal axial decompression but also anterior or posterior decompression. For example, in a patient recovering from disc surgery, the spacer device may be angled toward lordosis to take pressure off the intervertebral disc temporarily. Likewise the spacer device may be angled toward kyphosis to temporarily reduce pressure on a recovering facet joint.

In another alternative embodiment, the material of the spacer device may be completely or partially rigid. A sheath may be also surround the spacer device to limit direct contact between the spacer device and the surrounding tissue. The sheath may also serve to contain wear debris and limit over stretching of the spacer device.

Figure 5:
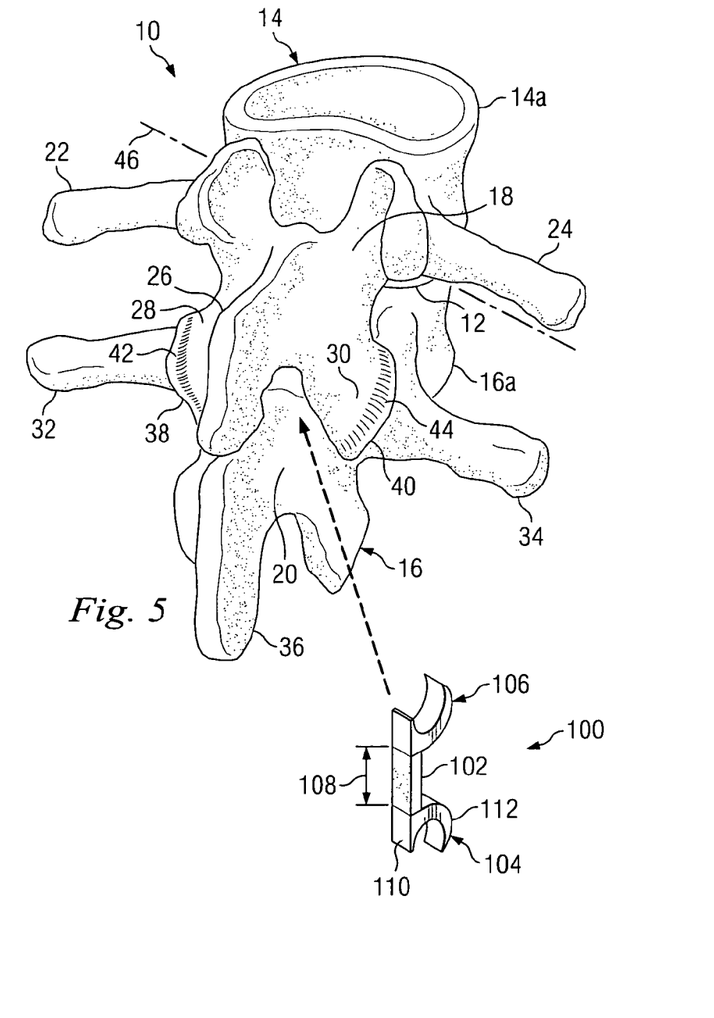
FIG. 5 is a perspective view of a vertebral column with an inter-laminar spacer system according to one embodiment of the present disclosure.
Figure 6:
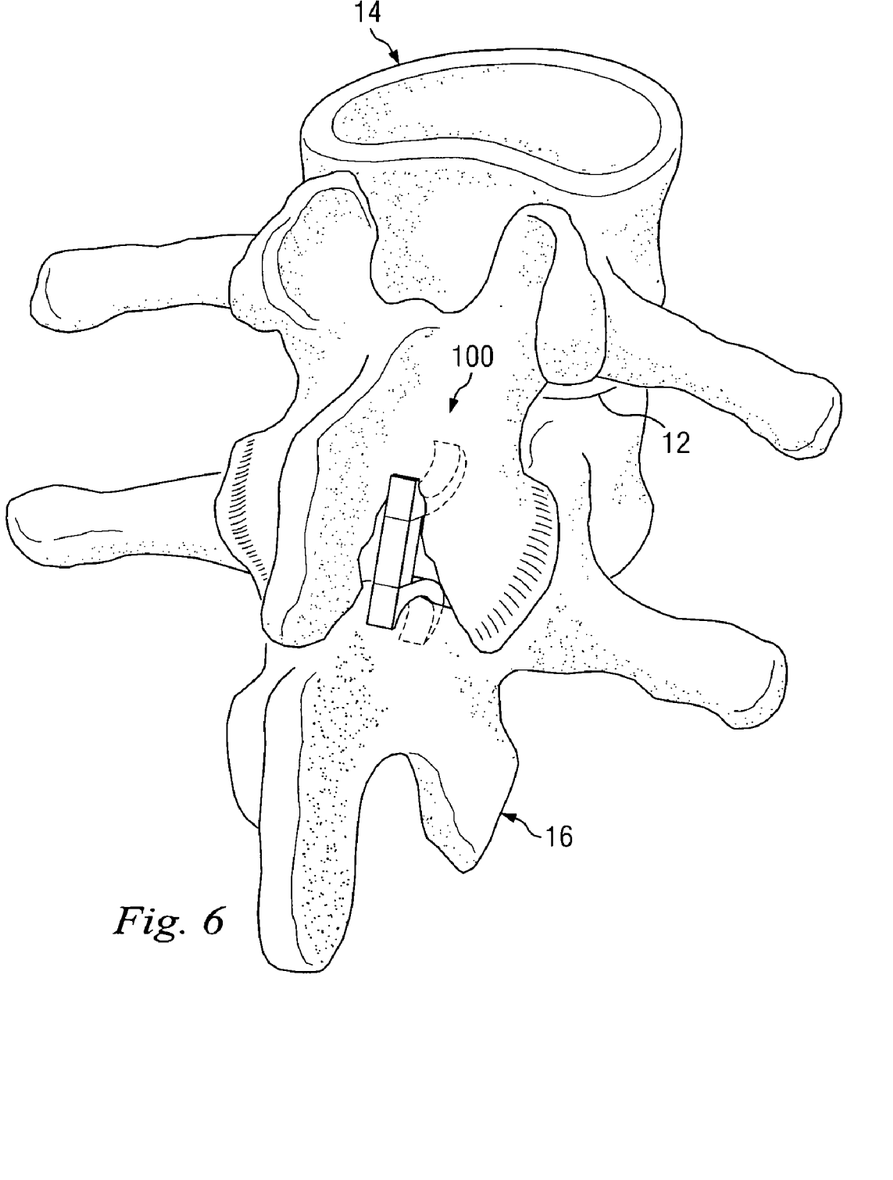
FIG. 6 is an assembled perspective view of the spacer system of FIG. 5.

Referring now to FIGS. 5 and 6, in one embodiment, a spacer system 100 may be used to support the laminae 18, 20; decompress the disc 12 and the facet joint 44; and/or relieve stenosis. The spacer system 100 includes a spacer device 102 which may be monolithically formed of an elastic, multi-directionally flexible material such as silicone, polyurethane, or hydrogel. The spacer device 102 may have a wider mid-section and may taper slightly toward the ends. The spacer device may have a height 108 which may be slightly greater than the inter-laminar space between the processes 18, 20 when the vertebra 14, 16 are in a natural position. For example, the cervical and lumbar regions of the vertebral column may be in lordosis when in a natural position.

The spacer system 100 further includes connection devices 104, 106 such as laminar hooks which are attached to the opposite ends of the spacer device 102. The laminar hook 104 may comprise an outer arm 110 and an inner arm 112. The laminar hooks 104, 106 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

A surgical procedure to implant the spacer system 100 may be relatively minimally invasive. Using a posterior, posterolateral, lateral, or other suitable approach, a small incision may be created in the patient's skin. The ligamentum flavum or other soft tissues may be mobilized and the laminae 18, 20 may be visualized directly or with radiographic assistance. The spacer device 102 may be compressed and the laminar hooks 104, 106 may be inserted between the laminae 18, 20. The spacer device 102 may then expand slightly so that hooks 104, 106 come into firm contact with the laminae 20, 18, respectively. The spacer device 102 may remain slightly compressed after implantation so that the hooks 104, 106 may continue to exert pressure on the laminae 20, 18, respectively, minimizing the opportunity for the spacer device 102 to be come dislodged. With the system 100 installed, the arms 110, 112 of the hook 104 may firmly contact the outer and inner faces, respectively, of the lamina 20. The hook 106 may similarly engage the lamina 18.

In certain anatomies, the spacer system 100 may be used alone to provide decompression to a single targeted facet joint or to relieve pressure on a particular side of the intervertebral disc, such as a herniation area. However, a second spacer system may also be installed on the opposite lateral side from the spacer system 100. The spacer system 100, when used in conjunction with a second spacer system, may provide more balanced support and equalized decompression.

The spacer system 100, as installed, may axially separate the vertebrae 14, 16, relieving pressure on the intervertebral disc 12 and the facet joint 44 and reducing wear and further degeneration. The spacer device 102 may also dampen the forces on the intervertebral disc 12 and facet joint 44 during motions such as flexion and extension. Because the spacer device 102 may be positioned relatively close to the natural axis of flexion 46, the spacer system 100 may be less likely to induce kyphosis as compared to systems that rely upon interspinous process devices to provide decompression. Additionally, the system 100 may installed with less dissection than the inter-spinous process devices of the prior art. Furthermore, an inter-laminar system can be used on each lateral side of the vertebrae 14, 16, and may provide greater and more balanced decompression than the single inter-spinous process devices of the prior art.

In an alternative embodiment, the laminar hooks may have a spring action which draws the arms together to engage the lamina, or the hooks may have a vise mechanism which draws the arms together to engage the lamina. This holding action, together with the flexibility of the device 102, may minimize friction and the associated material and bone wear.

In still another alternative, the spacer device may be formed of a rigid material such as those listed above for the laminar hooks. A rigid spacer device may be height adjustable such that a decreased height may be set to provide easy access for the laminar hooks, and an increased height may be set to bring the hooks into firm contact with the laminar walls.

In still another alternative embodiment, the connection devices may attach to other posterior bones such as the adjacent articular or spinous process. A connection device such as the cabling system 72 described above may also be used to connect the spacer device between the laminae. For example, a cable could extend around the lamina, through the spinal foramen to tether the spacer device to the lamina.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method of decompressing a spinal joint, the method comprising:
    accessing an interlaminar space between adjacent upper and lower laminae of a single interlaminar level;
    inserting a spacer system having first and second connection devices into the interlaminar space;
    engaging the upper and lower laminae with the first and second connection devices respectively such that the first connection device engages an inferior surface of the upper lamina and the second connection device engages a superior surface of the lower lamina;
    wherein the first and second connection devices comprise first and second hooks, respectively, having first and second hook surfaces, respectively, facing in generally opposite directions;
    wherein the spacer system includes a central portion and the first and second hooks are connected to each other only through the central portion;
    wherein the central portion is laterally offset from a vertical axis defined by minimum points on the first and second hooks respectively such that after said inserting, the central portion is disposed posteriorly with respect to the laminae of the single interlaminar level.

2. The method of claim 1 wherein, when the spacer system is inserted in the interlaminar space, the central portion does not extend above the upper lamina or below the lower lamina of the single interlaminar level.

3. The method of claim 2 wherein said inserting comprises compressing the central portion to elastically deform the central portion.

4. The method of claim 3 further comprising maintaining the central portion in a compressed state while the spinal joint is in a natural position.

5. The method of claim 4 wherein said maintaining the spacer component in a compressed state comprises the spacer system providing a decompressive force against the inferior surface of the upper lamina and the superior surface of the lower lamina after said insertion.

6. The method of claim 1 wherein said inserting comprises compressing the central portion to elastically deform the central portion.

7. The method of claim 6 further comprising maintaining the central portion in a compressed state while the spinal joint is in a natural position.

8. The method of claim 7 wherein said maintaining the spacer component in a compressed state comprises the spacer system providing a decompressive force against the inferior surface of the upper lamina and the superior surface of the lower lamina after said insertion.

9. The method of claim 1:
wherein said inserting the spacer comprises:
compressing the spacer system to a first compressed state;
inserting the spacer system in the first compressed state into the interlaminar space between the upper and lower laminae;
wherein engaging the upper and lower laminae comprises expanding the spacer system to a second compressed state.

10. The method of claim 1 wherein said engaging the upper and lower laminae comprises:
engaging the first hook surface with both an inferior surface and a posterior surface of the upper lamina;
engaging the second hook surface with both a superior surface and a posterior surface of the lower lamina.

11. The method of claim 2:
wherein said inserting the spacer comprises:
compressing the spacer system to a first compressed state;
inserting the spacer system in the first compressed state into the interlaminar space between the upper and lower laminae;
wherein engaging the upper and lower laminae comprises expanding the spacer system to a second compressed state.

12. The method of claim 2 wherein said engaging the upper and lower laminae comprises:
engaging the first hook surface with both an inferior surface and a posterior surface of the upper lamina;
engaging the second hook surface with both a superior surface and a posterior surface of the lower lamina.

* * * * *